United States Patent [19]

Koch et al.

[11] Patent Number: 4,855,309
[45] Date of Patent: Aug. 8, 1989

[54] PYRIDINE DERIVATIVES, AGENTS CONTAINING SAME, AND THE USE THEREOF AS PESTICIDES

[75] Inventors: Volker Koch, Kelkheim; Andreas Fuss, Karlstein; Werner Bonin, Kelkheim; Werner Knauf, Eppstein/Taunus; Anna Waltersdorfer, Frankfurt am Main, all of Fed. Rep. of Germany

[73] Assignee: Hoechst Aktiengesellschaft, Frankfurt am Main, Fed. Rep. of Germany

[21] Appl. No.: 944,323

[22] Filed: Dec. 19, 1986

[30] Foreign Application Priority Data

Dec. 21, 1985 [DE] Fed. Rep. of Germany ....... 3545569

[51] Int. Cl.[4] .................... A01N 43/10; C07D 213/65
[52] U.S. Cl. ..................................... 514/346; 514/89; 514/218; 514/229.2; 514/229.3; 514/274; 514/341; 514/342; 514/222.5; 540/492; 544/8; 544/67; 544/310; 546/24; 546/277; 546/278; 546/291
[58] Field of Search .................. 546/291, 24; 514/346, 514/89

[56] References Cited

FOREIGN PATENT DOCUMENTS

| | | |
|---|---|---|
| 0109211 | 5/1984 | European Pat. Off. . |
| 0138756 | 4/1985 | European Pat. Off. . |
| 138772 | 4/1985 | European Pat. Off. . |
| 2818830 | 8/1979 | Fed. Rep. of Germany . |
| 3240975 | 5/1983 | Fed. Rep. of Germany . |

OTHER PUBLICATIONS

C. Hensch, "Aromatic' Substituent Constants for Structure-Activity Correlations", *J. Med. Chem.*, 16 (11), 1207–1216 (1973).

*Primary Examiner*—Richard L. Raymond
*Attorney, Agent, or Firm*—Curtis, Morris & Safford

[57] ABSTRACT

The compounds of the formula (I)

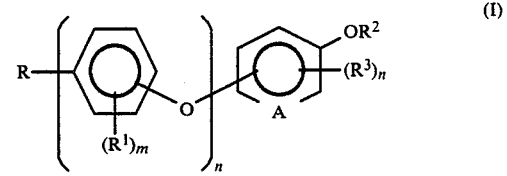

in which
A denotes N or N→0,
R denotes a radical of the formula $R^4$—$CY^1$—$NR^5$—$CY^2$—$NR^6$—,

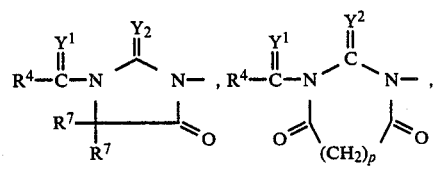

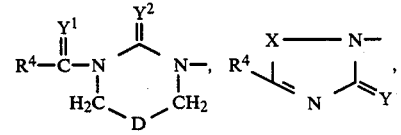

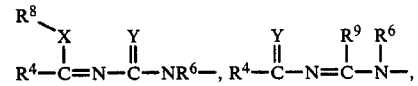

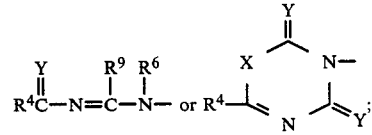

$R^1$ denotes halogen, alkyl, alkenyl, alkynyl, alkoxy, alkoxycarbonyl or alkylcarbonyl, where these radicals may be halogenated, nitro, cyano or carboxyl, $R^2$ denotes halogenated alkoxy, halogenated alkenyloxy or halogenated alkynloxy, $R^3$ denotes halogen, n denotes 0, 1 or 2, m denotes 0, 1, 2 or 3, and p denotes 0 or 1, and also the salts thereof, are advantageously suitable for combating noxious insects, acarides, nematodes or mollusks.

7 Claims, No Drawings

PYRIDINE DERIVATIVES, AGENTS CONTAINING SAME, AND THE USE THEREOF AS PESTICIDES

EP-A No. 109,211, DE-A No. 2,810,830 and EP-A No. 138,756 disclose pyridine-containing imidates, benzoylureas and oxadiazinediones for combating animal pests in plant protection. New pyridine derivatives having advantageous actions against plant pests have been found.

The present invention therefore relates to the compounds of the general formula (I)

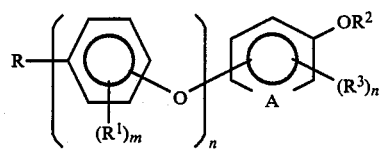

in which
A denotes N or N→O,
R denotes a radical of the formulae

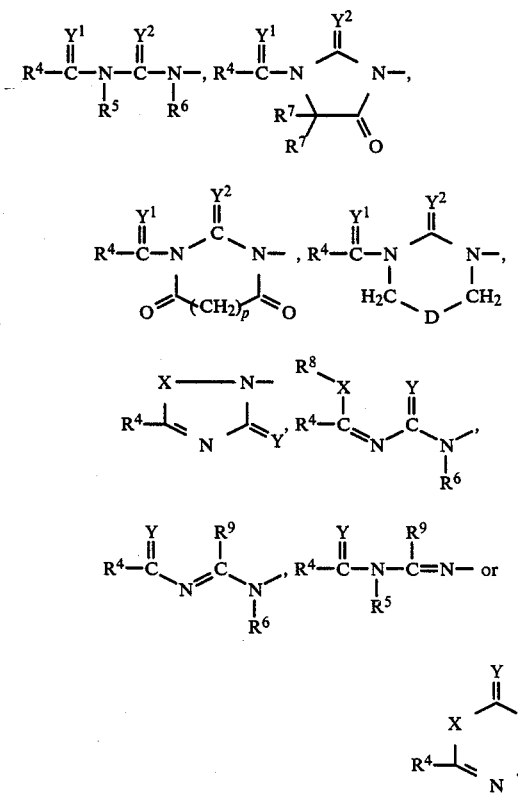

$R^1$ in each case independently of one another, denote halogen, ($C_1$-$C_6$)-alkyl, ($C_2$-$C_6$)-alkenyl, ($C_2$-$C_6$)-alkynyl, ($C_1$-$C_6$)-alkoxy, ($C_1$-$C_6$)-alkoxycarbonyl, ($C_1$-$C_6$-alkyl)-carbonyl, where the radicals may be mono- or polysubstituted by halogen, or denote nitro, cyano or carboxyl,
$R^2$ in each case independently of one another, denotes halogenated ($C_1$-$C_6$)-alkyl, halogenated ($C_2$-$C_6$)-alkenyl or halogenated ($C_2$-$C_6$)-alkynyl,
$R^3$ independently of one another, denote halogen, $R^4$ denotes phenyl which may be substituted by halogen, ($C_1$-$C_3$)-alkyl, ($C_1$-$C_3$)-alkoxy, halo($C_1$-$C_3$)-alkyl or halo($C_1$-$C_3$)-alkoxy,
$R^5$ denotes hydrogen, ($C_1$-$C_6$)-akoxy, ($C_1$-$C_6$)-alkylthio, benzyl, halogenated ($C_1$-$C_6$)-alkoxy, halogenated ($C_1$-$C_6$)-alkylthio or halogenated benzyl,
$R^6$ denotes H, ($C_1$-$C_6$)-alkyl, ($C_1$-$C_6$)-alkylthio or ($C_1$-$C_6$-alkylsulfonyl which all may be halogenated, pheylthio or phenylsulfonyl which is substituted by ($C_1$-$C_6$)-alkyl, ($C_1$-$C_6$)-alkoxy, ($C_1$-$C_6$)-alkoxycarbonyl, halogenated ($C_1$-$C_6$)-alkyl, halogenated ($C_1$-$C_6$)-alkoxy, halogenated ($C_1$-$C_4$)-alkoxycarbonyl, halogen, nitro or cyano, or denotes phosphoryl or thiophosphoryl which are both substituted by two radicals from the group comprising ($C_1$-$C_6$)-alkoxy, ($C_1$-$C_6$)-alkylthio, amino, ($C_1$-$C_6$)-alkylamino or di-($C_1$-$C_6$-alkyl)-amino,
$R^7$, independently of one another, denote H, halogen or ($C_1$-$C_3$)-alkyl,
$R^8$ denotes ($C_1$-$C_8$)-alkyl, ($C_2$-$C_8$)-alkenyl, ($C_2$-$C_8$)-alkynyl, phenyl or benzyl, which may all be halogenated,
$R^9$ denotes a radical of the formulae —$XR^8$, —S—S—$R^{10}$, benzimidazolyl, benztriazolyl or pyrazolyl, where these three radicals may be substituted by ($C_1$-$C_3$)-alkyl or halogen, or denotes triazolyl or imidazolyl which may both be substituted by ($C_1$-$C_3$)-alkyl,
$R^{10}$ denotes ($C_1$-$C_{18}$)-alkyl, ($C_3$-$C_8$)-cycloalkyl, phenyl($C_1$-$C_4$)-alkyl or phenyl, which may all be substituted by halogen, nitro or ($C_1$-$C_8$)-alkyl,
D denotes optionally branched $C_1$-$C_2$-alkylene, O or S,
X, Y, $Y^1$ and $Y^2$, independently of one another, denote O or S,
n, independently of one another, denote 0, 1 or 2,
m denotes 0, 1, 2 or 3, and
p denotes 0 or 1, and also the agriculturally acceptable salts.

The salts can be formed, for example, in the case of $R^1$=carboxyl or $R^5$=H. Suitable salts are, in particular, alkali metal salts, alkaline earth metal salts, ammonium salts or ammonium salts which are mono- to tetrasubstituted by organic radicals such as alkyl or hydroxyalkyl.

When n is 1 (for the phenoxy radical), R is preferably oriented in the para-position to the phenoxy oxygen. When n is 0, the R radical is bonded directly to the heterocycle of the formula I. The phenoxy radical or R is preferably orientated in the neighboring position to the ring atom A.

Preferred compounds of the formula I are those in which
A denotes N,
R denotes a radical of the formulae

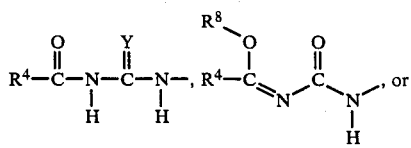

-continued

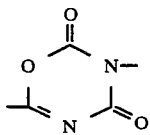

$R^1$, in each case independently of one another, denote halogen, ($C_1$–$C_6$)-alkyl or ($C_1$–$C_6$)-alkoxycarbonyl, where the radicals may be mono- or polysubstituted by halogen, $R^2$, in each case independently of one another, denote halogenated ($C_1$–$C_6$)-alkyl, halogenated ($C_2$–$C_6$)-alkenyl or halogenated ($C_2$–$C_6$)-alkynyl, $R^3$, independently of one another, denote halogen, $R^4$ denotes phenyl which may be substituted by halogen, ($C_1$–$C_3$)-alkyl, ($C_1$–$C_3$)-alkoxy, halo($C_1$–$C_3$)-alkyl or halo($C_1$–$C_3$)-alkoxy, $R^8$ denotes ($C_1$–$C_6$)-alkyl which may be halogenated, X, independently of one another, denote O or S, n, in the case of the phenoxy radical, denotes 0 or 1 and, in the case of the $R^3$ radical, denotes 0, 1 or 2, and m denotes 0, 1, 2 or 3.

Particularly preferred compounds of the formula I are those in which

A denotes N, $R^1$ denotes halogen in the 2, 3 or 5-position of the phenoxy ring relative to the position of R, or denotes halo($C_1$–$C_6$)-alkyl or ($C_1$–$C_3$)-alkoxycarbonyl, in each case in the 3 or 5-position of the phenoxy ring, $R^2$ denotes halo($C_1$–$C_3$)-alkoxy, $R^3$ denotes F, Cl or Br, and $R^4$ denotes phenyl which is substituted by halogen, particularly in the 2 or 6 position.

The invention also covers all stereoisomers, and mixtures thereof, of the compounds of the formula I, such as the E and Z isomers in the case of unsaturated structures, or optical isomers if centers of chirality occur. Furthermore, depending on the substitution, the compounds of the formula I can be present in tautomeric forms, which are likewise covered by the invention. The present invention also relates to processes for the preparation of the compounds of the formula I, wherein (a) for R=$R^4$—$CY^1$—$NR^5$—$CY^2$—$NR^6$—

(a1) a compound of the formula (II)

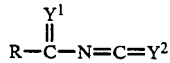

is reacted with a compound of the formula III

in which E denotes

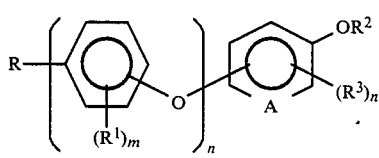

or (a2) a compound of the formula IV

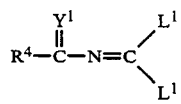

in which $L^1$, independently of one another, denote halogen, ($C_1$–$C_3$)-alkylthio, ($C_1$–$C_3$)-alkylsulfenyl or ($C_1$–$C_3$)-alkylsulfonyl, is reacted with a compound of the formula III, and subsequently with a compound of the formula $H_2Y$, or (a3) a compound of the formula V

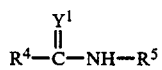

is reacted with a compound of the formula VIa $$Y^2=C=N-E \qquad (VIa)$$

or (a4) a compound of the formula V is reacted with a compound of the formula VIb

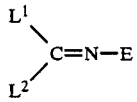

in which $L^2$ has the meaning of $L^1$ and additionally represents mercapto, and subsequently with a compound of the formula $H_2Y$, or (a5) a compound of the formula V is reacted with a compound of the formula VII

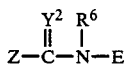

in which Z denotes ($C_1$–$C_6$)-alkoxy, ($C_1$–$C_6$)-alkylthio or benzyloxy, which may all be halogenated, triazolyl or imidazolyl, or a radical of the formula —$NHR^5$, or (b) for R=

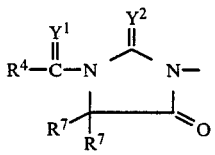

a compound of the formula VIII

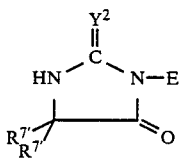

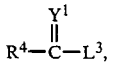

where $R^{7'}$ denotes H or $(C_1-C_3)$-alkyl, is reacted with a compound of the formula IX, where $L^3$ denotes a leaving group such as halogen or alkylthio, and the compounds obtained are, if appropriate, halogenated or alkylated, or (c) for R=

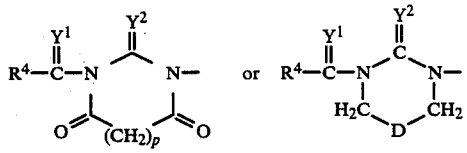

a compound, obtained according to process (a), of the formula I having $R^5$ and $R^6$=H is reacted with a compound Xa or Xb, in which $L^4$ denotes a leaving group such as halogen,

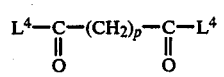     Xa

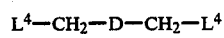     Xb or (d) for R=

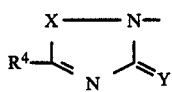

(d1) for X=O, a compound of the formula XI

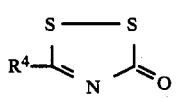     (XI)

HONH—E     (XII)

is reacted with a compound of the formula XII, and the resultant compound of the formula I, having Y=O, is thiolated in a known fashion, or (d2) for X=S, a compound, obtained according to (a), of the formula I having $Y^1$=S and $R^5$ and $R^6$=H, is cyclized, or (e) for R=

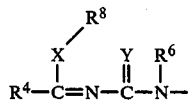

(e1) a compound of the formula XIII

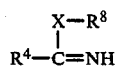     (XIII)

is reacted with a compound of the formula VIa or with a compound of the formula

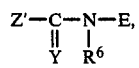

in which Z' has the meaning of Z, apart from —$NHR^5$, or (e2) a compound of the formula XIV

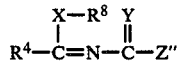     (XIV)

in which Z'' has the meaning of Z' or, additionally, represents halogen, is reacted with a compound of the formula III, or (f) for R=

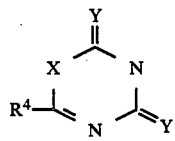

a compound of the formula II is reacted with a compound of the formula VIa, or (g) for R=

(g1) a compound of the formula XV

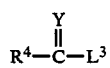     (XV)

is reacted with a compound of the formula XVI

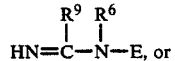     (XVI)

(g2) a compound of the formula XVII

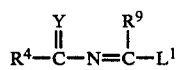     (XVII)

is reacted with a compound of the formula III, or (g3) for $R^9$=an abovementioned radical, apart from —X—$R^8$, a compound, obtained under (a), of the formula (I) having $Y^2$=S and $R^5$ and $R^6$=H is reacted with a compound of the formula $R^{9'}$—SO—$R^{9'}$, where $R^{9'}$ has the meaning of $R^9$, apart from —$XR^8$ and —S—S—$R^{10}$, or with a compound of the formula $L^5$—S—S—$R^{10}$, where $L^5$ denotes halogen, N-succinyl or an analogous radical, or (h) for R=

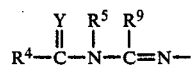

a compound of the formula XV is reacted with a compound of the formula XVIII

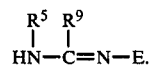     (XVIII)

The process steps mentioned under (a) to (h) are based on syntheses known to those skilled in the art.

For processes (a1), (a3) and (c), cf.: German Offenlegungsschrift No. 2,123,236

For processes (a2), cf.: German Offenlegungsschrift No. 2,123,236, and E. Kühle et al., Angew. Chem. 79, 671 ff (1967)

For process (a4), cf.: Houben-Weyl[(1)], Volume E 4, p. 1341 ff

[(1)]"Houben-Weyl", here and below, denotes: Houben-Weyl, Methoden der organischen Chemie [Methods of Organic Chemistry], Gerog-Thieme Verlag, Stuttgart.

For process (a5), cf.: Houben-Weyl, Volume E 4, p. 24 ff

For process (b), cf.: EP-A No. 116,103

For processes (d1) and (d2), cf.: EP-A No. 145,095

For processes (e1) and (e2), cf.: EP-A No. 135,894

For process (f), cf.: U.S. Pat. No. 4,150,158

For processes (g1) and (h), cf.: Houben-Weyl, Volume E 4, p. 593 ff

For process (g2), cf.: Houben-Weyl, Volume E 4, p. 1018 ff

For process (g3), cf.: EP-A No. 127,245.

The preparation of the starting compounds required for this purpose is likewise known in principle:

for (II), see Houben-Weyl, Volume E 4, p. 803 ff for (III), see Houben-Weyl, Volume 11/1, p. 9 ff for (IV), see Houben-Weyl, Volume E 4, p. 534 ff for (V), see Houben-Weyl, Volume E 5/1, p. 934 ff, p. 1141 ff, for (VIa) and (VIb), see German Patent Application P No. 35 45 570.5, "Neue Pyridin-Derivate und deren N-Oxide, Verfahren zu ihrer Herstellung und ihre Verwendung als Zwischenprodukte HOE 85/F 295)" [New pyridine derivatives and N-oxides thereof, processes for their preparation, and their use as intermediates (HOE 85/F 295)] Compounds VIa and VIb are prepared for example by converting the alcohol compounds where $R^2$ is H into the corresponding ether compounds by addition of an alkyl-, alkenyl- or alkynylhalogenide or by reacting the compounds analagous to VIa or VIb having a leaving group such as halogen, nitro, diazonium, alkylsulfonyl or pheylsulfonyl instead of the radical $R^2$ with an alkali-metal salt of a compound of the formula $OH—CH_2—R^{2'}$, whereby $R^{2'}$ corresponds to $R^2$. Processes for preparing the starting compounds of these reactions are known in the art, see A. Weissberger and E. C. Taylor, The Chemistry of Pyridine and Its Derivatives, Wiley, N.Y.

for (VII), see Houben-Weyl, Volume E 4, p. 142 ff

The compounds (VIII) can be prepared from the aminocarboxylic acids of the formula XIX

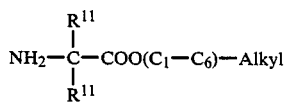
(XIX)

in which $R^{11}$, independently of one another, denote H or $(C_1-C_3)$-alkyl, by reaction with a compound of the formula VIa (having Y=O), cf. Chem. Rev. 46, 403 (1950), Houben-Weyl, E 5/1, p. 519.

For the preparation of (IX) and (XV), see Houben-Weyl, E 5/2, 587 ff For the preparation of (Xa), see Houben-Weyl, Volume 8, p. 365 ff, 463 ff For the preparation of (Xb), see Houben-Weyl, Volume 5/3 and 5/4

For the preparation of (XI), see Goerdeler, Chem. Ber. 99, p. 782 ff (1966), Chem. Ber. 106, p. 1496 (1973), Heterocycles 5, 189 (1976)

For the preparation of (XII), see German Patent Application P No. 35 45 570.5

For the preparation of (XIII), see DE-A No. 3,514,450

For the preparation of (XIV), see EP-A No. 135,894.

The compounds of the formula XVII or XVIII can be prepared from the compounds of the formulae XX and XXI

(XX)

(XXI)

by O- or S-alkylation, cf.

(XX) and XXI are prepared from the compounds XXII

(XXII)

according to Houben-Weyl, E 4, p. 534 ff

The compounds of the formula XXII are accessible from the amino compounds of the formula $NH_2—E$, which are described in German Patent Application No. P 35 45 570.5, by phosgenation, see Houben-Weyl, E 4, p. 738 ff, and subsequent functionalization, or from the thioisocyanates of the formula $S=C=N—E$ by a route known to those skilled in the art, see Houben-Weyl, E 4, p. 834 ff, or according to other known processes, see Houben-Weyl, Volume E IV.

The compounds of the formula XVII are prepared analogously to the known processes, see Houben-Weyl, E 4, p. 534 ff.

The active compounds are suitable for combating animal pests, in particular insects, arachnida, nematodes and mollusks, very particularly preferably for combating insects, encountered in agriculture, in forestry, in the protection of stored products and of materials, and in the hygiene field, and have good plant tolerance and favorable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderate, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloera vastatrix,* Pemphigus spp., *Pediculus humanus corporis,*

Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialuerodes vaporariorum, Aphis gossypii, Bravicornyne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Chemiatobia brumata, Lithocolletis blancardella, Hyponomeuta padella, Plutella maculipennis, Malacosoma neustria, Euproccis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Chroistoneura fumiferana, Clysia ambiguella, Homona magnanima* and *Tortrix viridana*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psyllides chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*. From the order of the Siphonaptera, for example, *Xenopsylla cheopis* and Ceratophyllus spp. From the order of the Arachnida, for example, *Scorpio maurus* and *Latrodectus mactans*.

From the class of the Gastropoda, for example, Deroceras Spp., Arion spp., Lymnaea spp., Galba spp., Succinea spp., Biophalaria spp., Bulinus spp. and Oncomelania spp..

From the class of the Bivalva, for example, Dreissena spp..

The invention also relates to agents which contain the compounds of the formula I, besides suitable formulation auxiliaries.

The agents according to the invention generally contain the active compounds of the formula I to the extent of 1–95% by weight. They can be used in the conventional preparations as wettable powders, emulsifiable concentrates, sprayable solutions, dusting agents or granules.

Wettable powders are preparations, uniformly dispersible in water, which contain, besides the active compound and in addition to a diluent or inert material, wetting agents, for example polyoxethylated alkylphenols, polyoxethylated fatty alcohols, alkyl- or alkylphenolsulfonates, and dispersing agents, for example sodium ligninsulfonate, sodium 2,2'-dinaphthylmethane-6,6'-disulfonate, sodium dibutylnaphthalenesulfonate, or sodium oleylmethyltaurinate.

Emulsifiable concentrates are prepared by dissolving the active compound in an organic solvent, for example butanol, cyclohexanone, dimethylformamide, xylene or higher-boiling aromatics or hydrocarbons, with addition of one or more emulsifiers. As emulsifiers, the following can be used, for example: calcium salts of alkylarylsulfonates, such as Ca dodecylbenzenesulfonate, or non-ionic emulsifiers such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents are obtained by grinding the active compound with finely divided solid substances, for example talcum, natural clays such as kaolin, bentonite, poryphillite or diatomaceous earth. Granules can be prepared either by atomizing the active compound onto adsorptive, granulated inert material or by applying active compound concentrates onto the surface of carrier materials such as sand or kaolinites, or of granulated inert material by means of adhesives, for example polyvinyl alcohol or sodium polyacrylate, or alternatively mineral oils. Suitable active compounds can also be prepared in the fashion conventional for the preparation of fertilizer granules—if desired as a mixture with fertilizers.

The active compounds according to the invention, partcularly those of the examples shown, may be present in their commercially available formulation, and in the application forms prepared from these formulations, as a mixture with other active compounds, such as insecticides, baits, sterilizing agents, acaricides, nematicides, fungicides, growth regulators or herbicides. The insecticides include, for example, phosphates, carbamates, carbonates, formamidines, tin compounds and substances produced by microorganisms, inter alia.

Preferred mixture components are 1. from the group comprising the phosphorus compounds acephate, azamethiphos, azinphos-ethyl, azinphosmethyl, bromophos, bromophos-ethyl, chlorfenvinphos, chlormephos, 1-(4-clorphenyl-4-(O-ethyl,S-propyl)phosphoryloxypyrazol (TIA 230), chlorpyrifos, chlorpyriphosmethyl, demeton, demeton-S-methyl, demeton-S-methyl sulphone, dialifos, diazinon, dichlorvos, dicrotophos, dimethoate, disulfoton, EPN, ethion, ethoprophos, etrimfos, famphur, fenamiphos, fenitrothion, fensulfothion, fenthion, fonofos, formothion, heptenophos, isazophos, isofenphos, isothioate, isoxathion, malathion, mephosfolan, methacrifos, methamidophos, methidathion, salithion, mevinphos, monocrotophos, naled, omethoate, oxydemeton-methyl, parathion, parathionmethyl, phenthoate phorate, phosalone, phosfolan, phosmet, phosphamidon, phoxim, pirimophosethyl, pirimiphosmethyl, profenofos, propaphos, propetamphos, prothiofos, pyridapenthion, quinalphos, sulprofos, temephos, terbufos, tetraclorvinphos, thiometon, triazophos, trichlorphon, vamidothion;

2. from the group comprising the carbamates aldicarb, 2-sec-butylphenylmethylcarbamte (BPMC), carbaryl, carbofuran, carbosulfan, cloethocarb, 2,3-dihydro-2,2-dimethyl-7-benzofuranyl-N-(isopropyl)-N-(carboethoxyethyl)amino)thiomethylcarbamate (OK-174), ethiofencarb, furathiocarb, isoprocarb, methomyl, 5-methyl-m-cumenylbutyryl)methyl)carbamate, oxamyl, piromicarb, propoxur, thiocarb, thifanox, ethyl 4,6,9-triaza-4-benzyl-6,10-dimethyl-8-oxa-7-oxo-5,11-dithia-9-dodecenoate (OK 135), 1-methylthio-(ethylideneamino)-N-methyl-N-(morpholinothio)carbamate (UC 51717);

3. from the group comprising the carboxylates allethrin, alphametrin, 5-benzyl-3-furylmethyl(E)-(1R)-cis-2,2-dimethyl-3-(2-oxothiolan-3-ylidenemethyl)cyclopropanecarboxylate, bioallethrin, bioallethrin((S)-cyclopentyl isomer), bioresmethrin, biphenate (FMC 54800), α-cyano-3'-phenoxybenzyl-2-(4-ethoxyphenyl) 2,2-dichlorocyclopyranecarboxylate (NK 8116, GH 414), (RS)-1-cyano-1-(6-phenoxy-2-pyridyl)methyl(1RS)-trans-3-(4-tert.butylphenyl) 2,2-dimethylcyclopropanecarboxylate (NCI 85193), cyfluthrin, cyhalothrin, cypermethrin, deltamethrin, empenthrin, esfenvalerate, 5-(4-(4-(4-ethoxyphenyl)-4-methylpentyl)-2-fluoro-1,3-diphenyl ether (MTI 800), 3-(2-(4-ethoxyphenyl-2-methylpropoxymethyl)-1,3-diphenyl ether (MTI 500), fenfluthrin, fenpropathrin, fenvalerate, flucythrinate, flumethrin, fluralinate (disomers), permethrin, phenothrin ((R)-isomers), pyrethrins (natural products), resmethrin, tetramethrin, tralomethrin;

4. from the group comprising the amidines amitraz, chlordimeform;

5. from the group comprising the tin compounds cyhexatin, fenbutatin oxide;

6. others abamectin, *Bacillus thuringiensis*, bensultap, binapacryl, bromopropylate, buprofezin, camphechlor, cartap, chlorbenzialate, chlorfluazuron, 2-(4-chlorophenyl)-4,5-diphenylthiophene (UBI-T 930), clofentezine, 2-naphthylmethyl cyclopropanecarboxylate (Ro 12-0470), cyromazin, DDT, dicofol, N-(3,5-dichloro-2,4-difluorophenyl)amino)carbonyl)-2,6-difluorobenzamide (CME 134), N-(3,5-dichloro-4-(1,1,2,2-tetrafluoroethoxy)phenyl)amino)carbonyl)-2,6-difluorobenzamide (XRD 473), diflubenzuron, N-(2,3-dihydro-3-methyl-1,3-thiazol-2-ylidene)2,4-xylidine, dinobuton, dinocap, endosulfan, fenoxycarb, fenthiocarb, flubenzimine, gamma-HCH, hexythiazox, ivermectin, 2-nitromethyl-4,5-dihydro-6H-thiazine (SD 52618), 2-nitromethyl-3,4-dihydrothiazole (SD 35651), propargite, tetradifon, tetrahydro-5,5-dimethyl-2(1H)-pyrimidinone(3-(4-trifluoromethyl)phenyl)-1-(2-(4-trifluoromethyl)phenyl-)ethenyl-2-propylidene)hydrazone (AC 217300), tetrasul, thiocyclam, triflumuron, nuclear polyhedrosis and granulosis viruses.

The active compound content of the use forms prepared from the commercially available formulations can vary within broad ranges. The active compound concentration of the use forms can be from 0.0000001 to 100% by weight of active compound, preferably between 0.00001 and 1% by weight.

Application is effected in a conventional fashion, matched to the use forms.

The active compounds according to the invention are also suitable for combating ecto- and endoparasites, for example helminths or ectoparasitizing insects, in the veterinary medicine area or in the area of animal husbandry.

The active compounds according to the invention are applied in a known fashion, such as by oral application in the form of, for example, tablets, capsules, potions or granules, by dermal application in the form of, for example, dipping, spraying, pouring-on and spotting-on and powdering, and also by parenteral application in the form of, for example, injection.

The novel compounds, according to the invention, of the formula I can accordingly also be employed particularly advantageously in livestock husbandry (for example cattle, sheep, pigs and poultry such as chickens, geese etc.). In a preferred embodiment of the invention, the novel compounds, if appropriate in suitable formulations (cf. above) and if appropriate with the drinking water or fee, are administered orally to the animals. Since excretion in the droppings occurs in an effective fashion, the development of insects in the animal droppings can be prevented very simply in this fashion. The dosages and formulations suitable in each case are particularly dependent on the type and stage of development of the productive animals and also on the degree of infestation of the insects, and can easily be determined and fixed by conventional methods. In the case of cattle, the novel compounds can be employed, for example, in dosages of 0.01 to 1 mg/kg of body weight.

The following examples serve to illustrate the invention.

A. Formulation Examples (a) A dusting agent is obtained by mixing 10 parts by weight of active compound and 90 parts by weight of talc as inert material and comminuting in a hammer mill.

(b) A wettable powder which is easily dispersible in water is obtained by mixing 25 parts by weight of active compound, 65 parts by weight of kaolin-containing quartz as inert material, 10 parts by weight of potassium ligninsulfonate and 1 part by weight of sodium oleoylmethyltaurinate as wetting and dispersing agent, and grinding in a pin disk mill.

(c) A dispersion concentrate which is easily dispersible in water is prepared by mixing 20 parts by weight of active compound with 6 parts by weight of alkylphenol polyglycol ether (Triton X 207), 3 parts by weight of isotridecanol polyglycol ether (8 EO) and 71 parts by weight of paraffinic mineral oil (boiling range, for example, about 255° to above 377° C.), and grinding in a ball mill to a fineness of below 5 microns.

(d) An emulsifiable concentrate can be prepared from 15 parts by weight of active compound, 75 parts by weight of cyclohexanone as solvent and 10 parts by weight of oxethylated nonylphenol (10 EO) as emulsifier.

(e) A granulate can be prepared from 2 to 15 parts by weight of active compound and an inert granulate carrier material such as attapulgite, granulated pumice and/or quartz sand.

B. Chemical Examples

EXAMPLE 1

N-(4-(3-Chloro-5-difluoromethoxy-2-pyridyloxy)-3,5-dichlorophenyl)-N'-(2,6-difluorobenzoylurea)

1.27 g (3 mmol) of 4-(3-chloro-5-difluoromethoxy-2-pyridyloxy)-3,5-dichloroaniline and 0.56 g (3 mmol) of freshly distilled 2,6-difluorobenzoyl isocyanate were stirred for 5 hours at room temperature, with the exclusion of moisture, and the solid formed was stirred with 10 ml of absolute n-heptane, filtered off under suction and recrystallized from toluene.

Yield: 1.67 g (92%).
Melting point: 200°–201° C.

EXAMPLE 2

N-4-(3-Chloro-5-(2-chloro-1,1,2-trifluoroethoxy)-2-pyridyloxy)-3,5-dichlorophenyl)-N'-2,6-difluorobenzoylurea This compound was prepared analogously to the procedure described in Example 1.
Melting point: 190°–192° C.

Example 3

Ethyl N-((4-(3-chloro-5-difluoromethoxy-2-pyridyloxy)-3,5-dichlorophenyl)carbamoyl)-2,6-difluorobenzocarboximidate 0.8 g (2.2 mmol) of 4-(3-chloro-5-difluoromethoxy-2-pyridyloxy)-3,5-dichlorophenyl isocyanate and 0.4 g (2.2 mmol) of ethyl 2,6-difluorobenzocarboximidate were stirred for 2 hours at room temperature with the exclusion of moisture, and the solid formed was stirred with 5 ml of absolute n-heptane, filtered off under suction and recrystallized from n-heptane.

Yield: 1.0 g (83%).
Melting point: 135°–137° C.

EXAMPLE 4

5-(4-(3-Chloro-5-difluoromethoxy-2-pyridyloxy)-3,5-dichlorophenyl)-2-(2,6-difluorophenyl)-6H-1,3,5-oxadiazine-4,6-dione 0.8 g (2.2 mmol) of 4-(3-chloro-5-difluoromethoxy-2-pyridyloxy)-3,5-dichlorophenyl isocyanate and 0.4 g (2.2 mmol) of 2,6-difluorobenzoyl isocyanate were stirred for 16 hours at 70° C. with the exclusion of moisture, and, after cooling, the solid formed was stirred with 5 ml of absolute n-heptane, filtered off under suction and recrystallized from cyclohexene/toluene; melting point 154°–6° C., yield: 86%.

The compounds in the tables below can be prepared as described in Examples 1–4.

TABLE 1

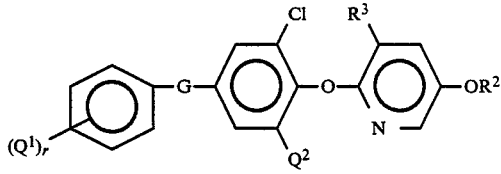

| Ex. No. | $(Q^1)_r$ | G | $Q^2$ | $R^2$ | $R^3$ | m.p. |
|---|---|---|---|---|---|---|
| 5 | 2-F | —C(O)—NH—C(O)—NH— | Cl | $CF_3$ | F | |
| 6 | 2,6$F_2$ | " | $CH_3$ | $CF_3$ | F | |
| 7 | 2,4,6-$Cl_3$ | " | Cl | $CF_2H$ | Cl | |
| 8 | 3,6-$F_2$ | —C(OC$_2$H$_5$)=N—C(O)—NH— | Cl | $CF_3$ | F | |
| 9 | 2,4-$Cl_2$ | " | $CH_3$ | H | Br | |
| 10 | 2-F | " | Cl | $CF_2CHFCF_3$ | H | |
| 11 | 2,6$F_2$—4-Cl | " | Cl | " | F | |
| 12 | 2-Cl | —C(O)—NH—C(O)—NH— | $CH_3$ | $CH_2CF_3$ | H | |
| 13 | 2F | oxadiazine-dione ring | Cl | $CF_2CF_3$ | F | |
| 14 | 2,6-$F_2$ | " | Cl | $CF_3$ | Cl | |
| 15 | 2F,6-Cl | " | Cl | $CF_2CHFBr$ | F | |

TABLE 2

[Structure: (Q¹)ᵣ-phenyl-C(O)-NH-C(O)-NH-phenyl(Q²)ₛ-O-pyridyl with R¹¹ and R¹⁰ substituents; positions 3 and 5 indicated on middle ring]

| Ex. No. | (Q¹)ᵣ | (Q²)ₛ | R¹⁰ | R¹¹ | m.p. (°C.) |
|---|---|---|---|---|---|
| 16 | 2-F | 2,5-Cl₂ | —OCHF₂ | Cl | |
| 17 | 2-Cl | 2,5-Cl₂ | " | Cl | 219–220 |
| 18 | 2,6-F₂ | 2,5-Cl₂ | " | Cl | 188–189 |
| 19 | 2,4-Cl₂ | 2,5-Cl₂ | " | Cl | |
| 20 | 2-OCH₃ | 2,5-Cl₂ | " | Cl | |
| 21 | 2-CH₃ | 2,5-Cl₂ | " | Cl | |
| 22 | 2-Cl | 2,5-Cl₂ | " | F | |
| 23 | 2,6-F₂ | 2,5-Cl₂ | " | F | |
| 24 | 2-Cl | 2,5-Cl₂ | " | Br | |
| 25 | 2-F | 2,5-Cl₂ | " | Br | |
| 26 | 2,6-F₂ | 2,5-Cl₂ | " | Br | |
| 27 | 2-Cl | 2,5-Cl₂ | —OCClF₂ | Cl | |
| 28 | 2,6-F₂ | 2,5-Cl₂ | —OCClF₂ | Cl | |
| 29 | 2-Cl | 2,5-Cl₂ | OCF₃ | Cl | |
| 30 | 2-F | 2,5-Cl₂ | " | Cl | |
| 31 | 2,6-F₂ | 2,5-Cl₂ | " | Cl | 191–193 |
| 32 | 2-Cl | 2,5-Cl₂ | " | F | |
| 33 | 2-F | 2,5-Cl₂ | " | F | |
| 34 | 2,6-F₂ | 2,5-Cl₂ | " | F | |
| 35 | 2-Cl | 2,5-Cl₂ | " | Br | |
| 36 | 2-F | 2,5-Cl₂ | " | Br | |
| 37 | 2,6-F₂ | 2,5-Cl₂ | " | Br | |
| 38 | 2-Cl | 2,5-Cl₂ | OCF₂CHF₂ | Cl | |
| 39 | 2-F | 2,5-Cl₂ | OCF₂CHF₂ | Cl | |
| 40 | 2,6-F₂ | 2,5-Cl₂ | OCF₂CHF₂ | Cl | 179–180 |
| 41 | 2-Cl | 2,5-Cl₂ | OCF₂CHF₂ | F | |
| 42 | 2-F | 2,5-Cl₂ | OCF₂CHF₂ | F | |
| 43 | 2,6-F₂ | 2,5-Cl₂ | —OCF₂CHF₂ | F | |
| 44 | 2-Cl | 2,5-Cl₂ | —OCF₂CHF₂ | Br | |
| 45 | 2-F | 2,5-Cl₂ | —OCF₂CHF₂ | Br | |
| 46 | 2,6-F₂ | 2,5-Cl₂ | —OCF₂CHF₂ | Br | |
| 47 | 2-Cl | 2,5-Cl₂ | —OCF₂CHClF₂ | Cl | 219–220 |
| 48 | 2,6-F₂ | 2,5-Cl₂ | —OCF₂CHClF₂ | Cl | 199–200 |
| 49 | 2-Cl | 2,5-Cl₂ | —OCF₂CHClF₂ | F | |
| 50 | 2,6-F₂ | 2,5-Cl₂ | —OCF₂CHClF₂ | F | |
| 51 | 2-Cl | 2,5-Cl₂ | —OCF₂CHClF₂ | Br | |
| 52 | 2,6-F₂ | 2,5-Cl₂ | —OCF₂CHClF₂ | Br | |
| 53 | 2,6-F₂ | 2,5-Cl₂ | —OCF₂CHBrF₂ | Cl | 185–186 |
| 54 | 2-Cl | 2,5-Cl₂ | —OCF₂CHFCF₃ | Cl | 192–193 |
| 55 | 2-F | 2,5-Cl₂ | —OCF₂CHFCF₃ | Cl | 183–184 |
| 56 | 2,6-F₂ | 2,5-Cl₂ | —OCF₂CHFCF₃ | Cl | 196–197 |
| 57 | 2-CH₃ | 2,5-Cl₂ | —OCF₂CHFCF₃ | Cl | |
| 58 | 2-OCH₃ | 2,5-Cl₂ | —OCF₂CHFCF₃ | Cl | |
| 59 | 2-Cl | 2,5-Cl₂ | —OCF₂CHFCF₃ | F | |
| 60 | 2-F | 2,5-Cl₂ | —OCF₂CHFCF₃ | F | |
| 61 | 2,6-F₂ | 2,5-Cl₂ | —OCH₂CHFCF₃ | F | |
| 62 | 2-Cl | 2,5-Cl₂ | —OCH₂CHFCF₃ | Br | |
| 63 | 2-F | 2,5-Cl₂ | —OCH₂CHFCF₃ | Br | |
| 64 | 2,6-F₂ | 2,5-Cl₂ | —OCH₂CHFCF₃ | Br | |
| 65 | 2-Cl | 2,5-Cl₂ | —OCH₂CH=CHCl | Cl | 132–133 |
| 66 | 2,6-F₂ | 2,5-Cl₂ | —OCH₂CH=CHCl | Cl | |
| 67 | 2-Cl | 2,5-Cl₂ | —OCH₂CCl=CHCl | Cl | 135–136 |
| 68 | 2,6-F₂ | 2,5-Cl₂ | —OCH₂CCl=CHCl | Cl | |
| 69 | 2-Cl | 2,5-Cl₂ | —OCH₂C≡C—Cl | Cl | |
| 70 | 2,6-F₂ | 2,5-Cl₂ | —OCH₂C≡C—Cl | Cl | 129–130 |
| 71 | 2-Cl | 3,5-Cl₂ | —OCHF₂ | Cl | 161–163 |
| 72 | 2-F | 3,5-Cl₂ | —OCHF₂ | Cl | 150–153 |
| 73 | 2-CH₃ | 3,5-Cl₂ | —OCHF₂ | Cl | |
| 74 | 2-OCH₃ | 3,5-Cl₂ | —OCHF₂ | Cl | |
| 75 | 2-Cl | 3,5-Cl₂ | —OCHF₂ | F | |
| 76 | 2-F | 3,5-Cl₂ | —OCHF₂ | F | |
| 77 | 2,6-F₂ | 3,5-Cl₂ | —OCHF₂ | F | |
| 78 | 2-Cl | 3,5-Cl₂ | —OCHF₂ | Br | |
| 79 | 2-F | 3,5-Cl₂ | —OCHF₂ | Br | |

TABLE 2-continued

[Structure: (Q¹)ᵣ-phenyl-C(O)-NH-C(O)-NH-phenyl(3,5-(Q²)ₛ)-O-pyridyl(R¹¹, R¹⁰)]

| Ex. No. | (Q¹)ᵣ | (Q²)ₛ | R¹⁰ | R¹¹ | m.p. (°C.) |
|---|---|---|---|---|---|
| 80 | 2,6-F₂ | 3,5-Cl₂ | —OCHF₂ | Br | |
| 81 | 2-Cl | 3,5-Cl₂ | —OCClF₂ | Cl | 233–235 |
| 82 | 2-F | 3,5-Cl₂ | —OCClF₂ | Cl | 178–179 |
| 83 | 2,6-F₂ | 3,5-Cl₂ | —OCClF₂ | Cl | 203–205 |
| 84 | 2-Cl | 3,5-Cl₂ | —OCClF₂ | F | |
| 85 | 2,6-F₂ | 3,5-Cl₂ | —OCClF₂ | F | |
| 86 | 2-Cl | 3,5-Cl₂ | —OCClF₂ | Br | |
| 87 | 2,6-F₂ | 3,5-Cl₂ | —OCClF₂ | Br | |
| 88 | 2-Cl | 3,5-Cl₂ | —OCF₃ | Cl | 217–218 |
| 89 | 2-F | 3,5-Cl₂ | —OCF₃ | Cl | 201–202 |
| 90 | 2,6-F₂ | 3,5-Cl₂ | —OCF₃ | Cl | 198–199 |
| 91 | 2-CH₃ | 3,5-Cl₂ | —OCF₃ | Cl | 212–213 |
| 92 | 2-OCH₃ | 3,5-Cl₂ | —OCF₃ | Cl | 179–180 |
| 93 | 2-Cl | 3,5-Cl₂ | —OCF₃ | F | |
| 94 | 2-F | 3,5-Cl₂ | —OCF₃ | F | |
| 95 | 2,6-F₂ | 3,5-Cl₂ | —OCF₃ | F | |
| 96 | 2-CH₃ | 3,5-Cl₂ | —OCF₃ | F | |
| 97 | 2-OCH₃ | 3,5-Cl₂ | —OCF₃ | F | |
| 98 | 2-Cl | 3,5-Cl₂ | —OCF₃ | Br | 185–186 |
| 99 | 2-F | 3,5-Cl₂ | —OCF₃ | Br | 177–178 |
| 100 | 2,6-F₂ | 3,5-Cl₂ | —OCF₃ | Br | 201–202 |
| 101 | 2-CH₃ | 3,5-Cl₂ | —OCF₃ | Br | |
| 102 | 2-OCH₃ | 3,5-Cl₂ | —OCF₃ | Br | |
| 103 | 2-Cl | 3,5-Cl₂ | —OCH₂CHF₂ | Cl | 221–223 |
| 104 | 2-F | 3,5-Cl₂ | —OCH₂CHF₂ | Cl | 164–165 |
| 105 | 2,6-F₂ | 3,5-Cl₂ | —OCH₂CHF₂ | Cl | 193–195 |
| 106 | 2-Cl | 3,5-Cl₂ | —OCH₂CHF₂ | F | |
| 107 | 2-F | 3,5-Cl₂ | —OCH₂CHF₂ | F | |
| 108 | 2,6-F₂ | 3,5-Cl₂ | —OCH₂CHF₂ | F | |
| 109 | 2-Cl | 3,5-Cl₂ | —OCH₂CHF₂ | Br | |
| 110 | 2-F | 3,5-Cl₂ | —OCH₂CHF₂ | Br | |
| 111 | 2,6-F₂ | 3,5-Cl₂ | —OCH₂CHF₂ | Br | |
| 112 | 2-Cl | 3,5-Cl₂ | —OCF₂CF₃ | Cl | |
| 113 | 2,6-F₂ | 3,5-Cl₂ | —OCF₂CF₃ | Cl | |
| 114 | 2-Cl | 3,5-Cl₂ | —OCF₂CCl₂F | Cl | |
| 115 | 2-F | 3,5-Cl₂ | —OCF₂CCl₂F | Cl | |
| 116 | 2-Cl | 3,5-Cl₂ | —OCF₂CHClF | Cl | 228–229 |
| 117 | 2-F | 3,5-Cl₂ | —OCF₂CHClF | Cl | 170–171 |
| 118 | 2,4-Cl₂ | 3,5-Cl₂ | —OCF₂CHClF | Cl | |
| 119 | 2-CH₃ | 3,5-Cl₂ | —OCF₂CHClF | Cl | |
| 120 | 2-OCH₃ | 3,5-Cl₂ | —OCF₂CHClF | Cl | |
| 121 | 2-Cl | 3,5-Cl₂ | —OCF₂CHClF | F | |
| 122 | 2,6-F₂ | 3,5-Cl₂ | —OCF₂CHClF | F | |
| 123 | 2-Cl | 3,5-Cl₂ | —OCF₂CHClF | Br | |
| 124 | 2,6-F₂ | 3,5-Cl₂ | —OCF₂CHClF | Br | |
| 125 | 2,6-F₂ | 3,5-Cl₂ | —OCF₂CHBrF | Cl | 191–192 |
| 126 | 2-Cl | 3,5-Cl₂ | —OCF₂CHFCF₃ | Cl | 216–217 |
| 127 | 2-F | 3,5-Cl₂ | —OCF₂CHFCF₃ | Cl | 178–179 |
| 128 | 2,6-F₂ | 3,5-Cl₂ | —OCF₂CHFCF₃ | Cl | 189–190 |
| 129 | 2-CH₃ | 3,5-Cl₂ | —OCF₂CHFCF₃ | Cl | |
| 130 | 2-OCH₃ | 3,5-Cl₂ | —OCF₂CHFCF₃ | Cl | |
| 131 | 2-Cl | 3,5-Cl₂ | —OCF₂CHFCF₃ | F | |
| 132 | 2-F | 3,5-Cl₂ | —OCF₂CHFCF₃ | F | |
| 133 | 2,6-F₂ | 3,5-Cl₂ | —OCF₂CHFCF₃ | F | |
| 134 | 2-Cl | 3,5-Cl₂ | —OCF₂CHFCF₃ | Br | |
| 135 | 2-F | 3,5-Cl₂ | —OCF₂CHFCF₃ | Br | |
| 136 | 2,6-F₂ | 3,5-Cl₂ | —OCF₂CHFCF₃ | Br | |
| 137 | 2-Cl | 3,5-Cl₂ | —OCH₂CH=CHCl | Cl | |
| 138 | 2-F | 3,5-Cl₂ | —OCH₂CH=CHCl | Cl | |
| 139 | 2,6-F₂ | 3,5-Cl₂ | —OCH₂CH=CHCl | Cl | 136–137 |
| 140 | 2-Cl | 3,5-Cl₂ | —OCH₂C(Cl)=CHCl | Cl | |
| 141 | 2-F | 3,5-Cl₂ | —OCH₂C(Cl)=CHCl | Cl | |

TABLE 2-continued

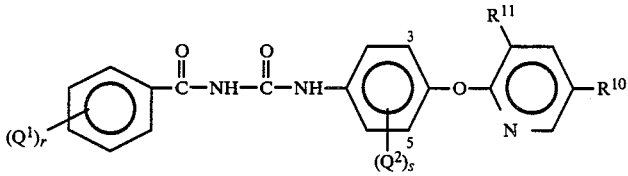

| Ex. No. | $(Q^1)_r$ | $(Q^2)_s$ | $R^{10}$ | $R^{11}$ | m.p. (°C.) |
|---|---|---|---|---|---|
| 142 | 2,6-$F_2$ | 3,5-$Cl_2$ | $-OCH_2C(Cl)=CHCl$ | Cl | 129–130 |
| 143 | 2-Cl | 3,5-$Cl_2$ | $-OCH_2C\equiv C-Cl$ | Cl | |
| 144 | 2,6-$F_2$ | 3,5-$Cl_2$ | $-OCH_2C\equiv C-Cl$ | Cl | 139–140 |
| 145 | 2-Cl | 3,5-$Cl_2$ | Cl | $OCHF_2$ | 183–184 |
| 146 | 2-F | 3,5-$Cl_2$ | Cl | $-OCHF_2$ | |
| 147 | 2,6-$F_2$ | 3,5-$Cl_2$ | Cl | $-OCHF_2$ | 219–220 |
| 148 | 2-Cl | 3,5-$Cl_2$ | Cl | $-OCF_2CHClF$ | 215–216 |
| 149 | 2,6-$F_2$ | 3,5-$Cl_2$ | Cl | $-OCF_2CHClF$ | 193–194 |
| 150 | 2-Cl | 3,5-$Cl_2$ | Cl | $-OCF_2CHF_2$ | |
| 151 | 2,6-$F_2$ | 3,5-$Cl_2$ | Cl | $-OCF_2CHF_2$ | |
| 152 | 2-Cl | 3,5-$Cl_2$ | Cl | $-OCF_2CHFCF_3$ | |
| 153 | 2,6-$F_2$ | 3,5-$Cl_2$ | Cl | $-OCF_2CHFCF_3$ | |
| 154 | 2-Cl | 3,5-$Cl_2$ | $-OCHF_2$ | H | |
| 155 | 2,6-$F_2$ | 3,5-$Cl_2$ | $-OCHF_2$ | H | |
| 156 | 2-Cl | 3,5-$Cl_2$ | $-OCF_3$ | H | |
| 157 | 2,6-$F_2$ | 3,5-$Cl_2$ | $-OCF_3$ | H | 173–174 |
| 158 | 2-Cl | 3,5-$Cl_2$ | $-OCF_2CHF_2$ | H | |
| 159 | 2,6-$F_2$ | 3,5-$Cl_2$ | $-OCF_2CHF_2$ | H | |
| 160 | 2-Cl | 3,5-$Cl_2$ | $-OCF_2CHFCF_3$ | H | 193–194 |
| 161 | 2,6-$F_2$ | 3,5-$Cl_2$ | $-OCF_2CHFCF_3$ | Cl | |
| 162 | 2-Cl | 3,5-$Cl_2$ | $-OCHF_2$ | Cl | |
| 163 | 2-F | 3,5-$Cl_2$;2-F | $-OCHF_2$ | Cl | |
| 164 | 2,6-$F_2$ | 3,5-$Cl_2$;2-F | $-OCHF_2$ | Cl | |
| 165 | 2-Cl | 3,5-$Cl_2$;2-F | $-OCF_3$ | Cl | |
| 166 | 2-F | 3,5-$Cl_2$;2-F | $-OCF_3$ | Cl | |
| 167 | 2,6-$F_2$ | 3,5-$Cl_2$;2-F | $-OCF_3$ | Cl | |
| 168 | 2-Cl | 3,5-$Cl_2$;2-F | $-OCF_2CHF_2$ | Cl | |
| 169 | 2,6-$F_2$ | 3,5-$Cl_2$;2-F | $-OCF_2CHF_2$ | Cl | |
| 170 | 2-Cl | 3,5-$Cl_2$;2-F | $-OCF_2CHFCF_3$ | Cl | |
| 171 | 2-F | 3,5-$Cl_2$;2-F | $-OCF_2CHFCF_3$ | Cl | |
| 172 | 2,6-$F_2$ | 3,5-$Cl_2$;2-F | $-OCF_2CHFCF_3$ | Cl | |
| 173 | 2-Cl | 2-Cl;5-$CF_3$ | $-OCHF_2$ | Cl | |
| 174 | 2-F | 2-Cl;5-$CF_3$ | $-OCHF_2$ | Cl | |
| 175 | 2,6-$F_2$ | 2-Cl;5-$CF_3$ | $-OCHF_2$ | Cl | 195–196 |
| 176 | 2-Cl | 2-Cl;5-$CF_3$ | $-OCF_3$ | Cl | |
| 177 | 2-F | 2-Cl;5-$CF_3$ | $-OCF_3$ | Cl | |
| 178 | 2,6-$F_2$ | 2-Cl;5-$CF_3$ | $-OCF_3$ | Cl | 201–203 |
| 179 | 2-Cl | 2-Cl;5-$CF_3$ | $-OCF_2CHF_2$ | Cl | |
| 180 | 2-F | 2-Cl;5-$CF_3$ | $-OCF_2CHF_2$ | Cl | |
| 181 | 2,6-$F_2$ | 2-Cl;5-$CF_3$ | $-OCF_2CHF_2$ | Cl | |
| 182 | 2,6-$F_2$ | 2-Cl;5-$CF_3$ | $-OCF_2CHClF$ | Cl | |
| 183 | 2-Cl | 2-Cl;5-$CF_3$ | $-OCF_2CHFCF_3$ | Cl | |
| 184 | 2-F | 2-Cl;5-$CF_3$ | $-OCF_2CHFCF_3$ | Cl | |
| 185 | 2,6-$F_2$ | 2-Cl;5-$CF_3$ | $-OCF_2CHFCF_3$ | Cl | 192–193 |
| 186 | 2-Cl | 3-$CF_3$ | $-OCHF_2$ | Cl | |
| 187 | 2-F | 3-$CF_3$ | $-OCHF_2$ | Cl | |
| 188 | 2,6-$F_2$ | 3-$CF_3$ | $-OCHF_2$ | Cl | |
| 189 | 2-Cl | 3-$CF_3$ | $-OCF_3$ | Cl | |
| 190 | 2-F | 3-$CF_3$ | $-OCF_3$ | Cl | |
| 191 | 2,6-$F_2$ | 3-$CF_3$ | $-OCF_3$ | Cl | |
| 192 | 2-Cl | 3-$CF_3$ | $-OCF_2CHF_2$ | Cl | |
| 193 | 2-F | 3-$CF_3$ | $-OCF_2CHF_2$ | Cl | |
| 194 | 2,6-$F_2$ | 3-$CF_3$ | $-OCF_2CHF_2$ | Cl | |
| 195 | 2-Cl | 3-$CF_3$ | $-OCF_2CHClF$ | Cl | |
| 196 | 2-F | 3-$CF_3$ | $-OCF_2CHClF$ | Cl | |
| 197 | 2,6-$F_2$ | 3-$CF_3$ | $-OCF_2CHClF$ | Cl | |
| 198 | 2-Cl | 3-$CF_3$ | $-OCF_2CHFCF_3$ | Cl | 192–194 |
| 199 | 2-F | 3-$CF_3$ | $-OCF_2CHFCF_3$ | Cl | |
| 200 | 2,6-$F_2$ | 3-$CF_3$ | $-OCF_2CHFCF_3$ | Cl | |
| 201 | 2-Cl | 3-$COOCH_3$ | $-OCHF_2$ | Cl | |
| 202 | 2-F | 3-$COOCH_3$ | $-OCHF_2$ | Cl | |
| 203 | 2,6-$F_2$ | 3-$COOCH_3$ | $-OCHF_2$ | Cl | |
| 204 | 2-Cl | 3-$COOCH_3$ | $-OCF_3$ | Cl | |
| 205 | 2-F | 3-$COOCH_3$ | $-OCF_3$ | Cl | |
| 206 | 2,6-$F_2$ | 3-$COOCH_3$ | $-OCF_3$ | Cl | 211–212 |
| 207 | 2-Cl | 3-$COOCH_3$ | $-OCF_2CHF_2$ | Cl | |
| 208 | 2-F | 3-$COOCH_3$ | $-OCF_2CHF_2$ | Cl | |
| 209 | 2,6-$F_2$ | 3-$COOCH_3$ | $-OCF_2CHF_2$ | Cl | |

TABLE 2-continued

Structure: (Q¹)ᵣ-phenyl-C(O)-NH-C(O)-NH-phenyl(3,5-(Q²)ₛ)-O-pyridyl(R¹¹, R¹⁰)

| Ex. No. | (Q¹)ᵣ | (Q²)ₛ | R¹⁰ | R¹¹ | m.p. (°C.) |
|---|---|---|---|---|---|
| 210 | 2-Cl | 3-COOCH₃ | —OCF₂CHClF | Cl | |
| 211 | 2-F | 3-COOCH₃ | —OCF₂CHClF | Cl | |
| 212 | 2,6-F₂ | 3-COOCH₃ | —OCF₂CHClF | Cl | |
| 213 | 2-Cl | 3-COOCH₃ | —OCF₂CHFCF₃ | Cl | |
| 214 | 2-F | 3-COOCH₃ | —OCF₂CHFCF₃ | Cl | |
| 215 | 2,6-F₂ | 3-COOCH₃ | —OCF₂CHFCF₃ | Cl | 203–204 |
| 216 | 2-Cl | 3-Cl;5-COOCH₃ | —OCHF₂ | Cl | |
| 217 | 2-F | 3-Cl;5-COOCH₃ | —OCHF₂ | Cl | |
| 218 | 2,6-F₂ | 3-Cl;5-COOCH₃ | —OCHF₂ | Cl | |
| 219 | 2-Cl | 3-Cl;5-COOCH₃ | —OCF₃ | Cl | |
| 220 | 2-F | 3-Cl;5-COOCH₃ | —OCF₃ | Cl | |
| 221 | 2,6-F₂ | 3-Cl;5-COOCH₃ | —OCF₃ | Cl | |
| 222 | 2-Cl | 3-Cl;5-COOCH₃ | —OCF₂CHF₂ | Cl | |
| 223 | 2-F | 3-Cl;5-COOCH₃ | —OCF₂CHF₂ | Cl | |
| 224 | 2,6-F₃ | 3-Cl;5-COOCH₃ | —OCF₂CHF₂ | Cl | |
| 225 | 2-Cl | 3-Cl;5-COOCH₃ | —OCF₂CHClF | Cl | |
| 226 | 2-F | 3-Cl;5-COOCH₃ | —OCF₂CHClF | Cl | |
| 227 | 2,6-F₂ | 3-Cl;5-COOCH₃ | —OCF₂CHClF | Cl | |
| 228 | 2-Cl | 3-Cl;5-COOCH₃ | —OCF₂CHFCF₃ | Cl | |
| 229 | 2-F | 3-Cl;5-COOCH₃ | —OCF₂CHFCF₃ | Cl | |
| 230 | 2,6-F₂ | 3-Cl;5-COOCH₃ | —OCF₂CHFCF₃ | Cl | |

TABLE 3

Structure: (Q¹)ᵣ-phenyl-C(O)-N⁻(K⁺)-C(O)-NH-phenyl(3,5-(Q²)ₛ)-O-pyridyl(R¹¹, R¹⁰)

| Ex. No. | (Q¹)ᵣ | K | (Q²)ₛ | R¹⁰ | R¹¹ | m.p. (°C.) |
|---|---|---|---|---|---|---|
| 231 | 2,6-F₂ | Na | 3,5-Cl₂ | —OCHF₂ | Cl | |
| 232 | " | Na | " | —OCF₃ | " | |
| 233 | " | Na | " | —OCF₂CHF₂ | " | |
| 234 | " | Na | " | —OCF₂CHClF | " | |
| 235 | " | Na | " | —OCF₂CHFCF₃ | " | 104–105 (decomp.) |
| 236 | " | N(C₄H₉)₄ | " | —OCHF₂ | " | |
| 237 | " | " | " | —OCF₃ | " | |
| 238 | " | " | " | —OCF₂CHF₂ | " | |
| 239 | " | " | " | —OCF₂CHClF | " | |
| 240 | " | " | " | —OCF₂CHFCF₃ | " | |

TABLE 4

Structure: (Q¹)ᵣ-phenyl-C(O)-NH-C(S)-NH-phenyl(3,5-(Q²)ₛ)-O-pyridyl(R¹¹, R¹⁰)

| Ex. No. | (Q¹)ᵣ | (Q²)ₛ | R¹⁰ | R¹¹ | m.p. (°C.) |
|---|---|---|---|---|---|
| 241 | 2-Cl | 3,5-Cl₂ | —OCHF₂ | Cl | |
| 242 | 2-F | " | " | " | |
| 243 | 2,6-F₂ | " | " | " | 228–230 |
| 244 | 2-Cl | " | —OCF₃ | " | |
| 245 | 2-F | " | " | " | |
| 246 | 2,6-F₂ | " | " | " | 219–220 |
| 247 | 2-Cl | " | —OCF₂CHF₂ | " | |
| 248 | 2-F | " | " | " | |
| 249 | 2,6-F₂ | " | " | " | 214–215 |
| 250 | 2-Cl | " | —OCF₂CHClF | " | |
| 251 | 2-F | " | " | " | |

TABLE 4-continued

Structure: (Q¹)ᵣ-phenyl-C(=O)-NH-C(=S)-NH-phenyl(Q²)ₛ-O-pyridyl(R¹¹, R¹⁰)

| Ex. No. | (Q¹)ᵣ | (Q²)ₛ | R¹⁰ | R¹¹ | m.p. (°C.) |
|---|---|---|---|---|---|
| 252 | 2,6-F₂ | " | " | " | |
| 253 | 2-Cl | " | —OCF₂CHFCF₃ | " | |
| 254 | 2-F | " | " | " | |
| 255 | 2,6-F₂ | " | " | " | 223–225 |

TABLE 5

Structure with OC₂H₅ and C=N-urea linker

| Ex. No. | (Q¹)ᵣ | (Q²)ₛ | R¹⁰ | R¹¹ | m.p. (°C.) |
|---|---|---|---|---|---|
| 256 | 2-Cl | 3,5-Cl₂ | —OCHF₂ | Cl | |
| 257 | 2-F | 3,5-Cl₂ | —OCHF₂ | Cl | |
| 258 | 2,4-Cl₂ | 3,5-Cl₂ | —OCHF₂ | Cl | |
| 259 | 2-Cl | 3,5-Cl₂ | —OCF₃ | Cl | 109–110 |
| 260 | 2-F | 3,5-Cl₂ | —OCF₃ | Cl | |
| 261 | 2,6-F₂ | 3,5-Cl₂ | —OCF₃ | Cl | 128–129 |
| 262 | 2-Cl | 3,5-Cl₂ | —OCF₂CHF₂ | Cl | |
| 263 | 2-F | 3,5-Cl₂ | —OCF₂CHF₂ | Cl | |
| 264 | 2,6-F₂ | 3,5-Cl₂ | —OCF₂CHF₂ | Cl | |
| 265 | 2-Cl | 3,5-Cl₂ | —OCF₂CHClF | Cl | |
| 266 | 2-F | 3,5-Cl₂ | —OCF₂CHClF | Cl | |
| 267 | 2,6-F₂ | 3,5-Cl₂ | —OCF₂CHClF | Cl | |
| 268 | 2-Cl | 3,5-Cl₂ | —OCF₂CHFCF₃ | Cl | 123–124 |
| 269 | 2-F | 3,5-Cl₂ | —OCF₂CHFCF₃ | Cl | |
| 270 | 2,6-F₂ | 3,5-Cl₂ | —OCF₂CHFCF₃ | Cl | 119–120 |

TABLE 6

Structure with oxadiazinedione ring

| Ex. No. | (Q¹)ᵣ | (Q²)ₛ | R¹⁰ | R¹¹ | m.p. (°C.) |
|---|---|---|---|---|---|
| 271 | 2-Cl | 3,5-Cl₂ | —OCHF₂ | Cl | |
| 272 | 2-F | 3,5-Cl₂ | —OCHF₂ | Cl | |
| 273 | 2,4-Cl₂ | 3,5-Cl₂ | —OCHF₂ | Cl | |
| 274 | 2-Cl | 3,5-Cl₂ | —OCF₃ | Cl | |
| 275 | 2-F | 3,5-Cl₂ | —OCF₃ | Cl | |
| 276 | 2,6-F₂ | 3,5-Cl₂ | —OCF₃ | Cl | 193–194 |
| 277 | 2-Cl | 3,5-Cl₂ | —OCF₂CHF₂ | Cl | |
| 278 | 2-F | 3,5-Cl₂ | —OCF₂CHF₂ | Cl | |
| 279 | 2,6-F₂ | 3,5-Cl₂ | —OCF₂CHF₂ | Cl | 179–180 |
| 280 | 2-Cl | 3,5-Cl₂ | —OCF₂CHClF | Cl | |
| 281 | 2-F | 3,5-Cl₂ | —OCF₂CHClF | Cl | |
| 282 | 2,6-F₂ | 3,5-Cl₂ | —OCF₂CHClF | Cl | |
| 283 | 2-Cl | 3,5-Cl₂ | —OCF₂CHFCF₃ | Cl | |
| 284 | 2-F | 3,5-Cl₂ | —OCF₂CHFCF₃ | Cl | |
| 285 | 2,6-F₂ | 3,5-Cl₂ | —OCF₂CHFCF₃ | Cl | 199–200 |

TABLE 7

Structure: (Q¹)ᵣ-phenyl-C(=O)-NH-C(=Y²)-NH-pyridyl(R¹¹, R¹⁰)

| Ex. No. | (Q¹)ᵣ | Y² | R¹⁰ | R¹¹ | m.p. (°C.) |
|---|---|---|---|---|---|
| 286 | 2-Cl | O | —OCHF₂ | Cl | |
| 287 | 2-F | O | —OCHF₂ | Cl | |
| 288 | 2,6-F₂ | O | —OCHF₂ | Cl | |
| 289 | 2-Cl | O | —OCF₃ | Cl | 129 |
| 290 | 2-F | O | —OCF₃ | Cl | 133–135 |
| 291 | 2,6-F₂ | O | —OCF₃ | Cl | 157 |
| 292 | 2-Cl | O | —OCF₂CHF₂ | Cl | |
| 293 | 2-F | O | —OCF₂CHF₂ | Cl | |
| 294 | 2,6-F₂ | O | —OCF₂CHF₂ | Cl | 154–155 |
| 295 | 2-Cl | O | —OCF₂CHClF | Cl | |
| 296 | 2-F | O | —OCF₂CHClF | Cl | |
| 297 | 2,6-F₂ | O | —OCF₂CHClF | Cl | |
| 298 | 2-Cl | O | —OCF₂CHFCF₃ | Cl | |
| 299 | 2-F | O | —OCF₂CHFCF₃ | Cl | |
| 300 | 2,6-F₂ | O | —OCF₂CHFCF₃ | Cl | |
| 301 | 2-Cl | O | —OCF₂CHFCF₃ | Br | |
| 302 | 2-F | O | —OCF₂CHFCF₃ | Br | |
| 303 | 2,6-F₂ | O | —OCF₂CHFCF₃ | Br | 131–133 |
| 304 | 2-Cl | O | H | —OCF₂CHFCF₃ | 164–165 |
| 305 | 2-F | O | H | —OCF₂CHFCF₃ | 130–131 |
| 306 | 2,6-F₂ | O | H | —OCF₂CHFCF₃ | 138 |
| 307 | 2-Cl | S | —OCHF₂ | Cl | |
| 308 | 2-F | S | —OCHF₂ | Cl | |

TABLE 7-continued

| Ex. No. | $(Q^1)_r$ | $Y^2$ | $R^{10}$ | $R^{11}$ | m.p. (°C.) |
|---|---|---|---|---|---|
| 309 | 2,6-F$_2$ | S | —OCHF$_2$ | Cl | |
| 310 | 2-Cl | S | —OCF$_3$ | Cl | |
| 311 | 2-F | S | —OCF$_3$ | Cl | |
| 312 | 2,6-F$_2$ | S | —OCF$_3$ | Cl | |
| 313 | 2-Cl | S | —OCF$_2$CHF$_2$ | Cl | |
| 314 | 2-F | S | —OCF$_2$CHF$_2$ | Cl | |
| 315 | 2,6-F$_2$ | S | —OCF$_2$CHF$_2$ | Cl | |
| 316 | 2-Cl | S | —OCF$_2$CHClF | Cl | |
| 317 | 2-F | S | —OCF$_2$CHClF | Cl | |
| 318 | 2,6-F$_2$ | S | —OCF$_2$CHClF | Cl | |
| 319 | 2-Cl | S | —OCF$_2$CHFCF$_3$ | Cl | |
| 320 | 2-F | S | —OCF$_2$CHFCF$_3$ | Cl | |
| 321 | 2,6-F$_2$ | S | —OCF$_2$CHFCF$_3$ | Cl | |

TABLE 8

| Ex. No. | $(Q^1)_r$ | $Y^2$ | $(Q_2)_s$ | $R^{10}$ | $R^{11}$ | m.p. (°C.) |
|---|---|---|---|---|---|---|
| 322 | 2-Cl | O | 2,5-Cl$_2$ | OCHF$_2$ | Cl | |
| 323 | 2-F | O | " | " | " | |
| 324 | 2,6-F$_2$ | O | " | " | " | |
| 325 | 2-Cl | O | " | OCF$_3$ | " | |
| 326 | 2-F | O | " | " | " | |
| 327 | 2,6-F$_2$ | O | " | " | " | |
| 328 | 2-Cl | O | " | OCF$_2$CHF$_2$ | " | |
| 339 | 2-F | O | " | " | " | |
| 330 | 2,6-F$_2$ | O | " | " | " | |
| 331 | 2-Cl | O | " | OCF$_2$CHClF | " | |
| 332 | 2-F | O | " | " | " | |
| 333 | 2,6-F$_2$ | O | " | " | " | |
| 334 | 2-Cl | O | " | OCF$_2$CHFCF$_3$ | " | |
| 335 | 2-F | O | " | " | " | |
| 336 | 2,6-F$_2$ | O | " | " | " | |
| 337 | 2-Cl | O | 3,5-Cl$_2$ | OCHF$_2$ | " | |
| 338 | 2-F | O | " | " | " | |
| 339 | 2,6-F$_2$ | O | " | " | " | |
| 340 | 2-Cl | O | " | OCF$_3$ | " | |
| 341 | 2-F | O | " | " | " | |
| 342 | 2,6-F$_2$ | O | " | " | " | |
| 343 | 2-Cl | O | " | OCF$_2$CHF$_2$ | " | |
| 344 | 2-F | O | 3,5-Cl$_2$ | " | " | |
| 345 | 2,6-F$_2$ | O | " | " | " | |
| 346 | 2-Cl | O | " | OCF$_2$CHClF | " | |
| 347 | 2-F | O | " | " | " | |
| 348 | 2,6-F$_2$ | O | 3,5-Cl$_2$ | OCF$_2$CHClF | Cl | |
| 349 | 2-Cl | O | " | OCF$_2$CHFCF$_3$ | " | |
| 350 | 2-F | O | " | " | " | |
| 351 | 2,6-F$_2$ | O | " | " | " | |
| 352 | 2-Cl | O | 3,5-Cl$_2$; 2-F | —OCHF$_2$ | " | |
| 353 | 2-F | O | " | " | " | |
| 354 | 2,6-F$_2$ | O | " | " | " | |
| 355 | 2-Cl | O | " | —OCF$_3$ | " | |
| 356 | 2-F | O | " | " | " | |
| 357 | 2,6-F$_2$ | O | " | " | " | |
| 358 | 2-Cl | O | " | —OCF$_2$CHF$_2$ | " | |
| 359 | 2-F | O | " | " | " | |
| 360 | 2,6-F$_2$ | O | " | " | " | |
| 361 | 2-Cl | O | " | —OCF$_2$CHClF | " | |
| 362 | 2-F | O | " | " | " | |
| 363 | 2,6-F$_2$ | O | " | " | " | |
| 364 | 2-Cl | O | " | OCF$_2$CHFCF$_3$ | " | |

TABLE 8-continued

| Ex. No. | $(Q^1)_r$ | $Y^2$ | $(Q^2)_s$ | $R^{10}$ | $R^{11}$ | m.p. (°C.) |
|---|---|---|---|---|---|---|
| 365 | 2-F | O | " | " | " | |
| 366 | 2,6-$F_2$ | O | " | " | " | |
| 367 | 2-Cl | O | 2-Cl, 5-$CF_3$ | —$OCHF_2$ | " | |
| 368 | 2-F | O | " | " | " | |
| 369 | 2,6-$F_2$ | O | " | " | " | |
| 370 | 2-Cl | O | " | —$OCF_3$ | " | |
| 371 | 2-F | O | " | " | " | |
| 372 | 2,6-$F_2$ | O | " | " | " | |
| 373 | 2-Cl | O | " | —$OCF_2CHF_2$ | " | |
| 374 | 2-F | O | " | " | " | |
| 375 | 2,6-$F_2$ | O | " | " | " | |
| 376 | 2-Cl | O | " | —$OCF_2CHClF$ | " | |
| 377 | 2-F | O | " | " | " | |
| 378 | 2,6-$F_2$ | O | " | " | " | |
| 379 | 2-Cl | O | 2-Cl, 5-$CF_3$ | —$OCF_2CHFCF_3$ | Cl | |
| 380 | 2-F | O | " | " | " | |
| 381 | 2,6-$F_2$ | O | " | " | " | |
| 382 | 2-Cl | O | 3-$CF_3$ | —$OCHF_2$ | " | |
| 383 | 2-F | O | " | " | " | |
| 384 | 2,6-$F_2$ | O | " | " | " | |
| 385 | 2-Cl | O | " | —$OCF_3$ | " | |
| 386 | 2-F | O | " | " | " | |
| 387 | 2,6-$F_2$ | O | " | " | " | |
| 388 | 2-Cl | O | " | —$OCF_2CHF_2$ | " | |
| 389 | 2-F | O | " | " | " | |
| 390 | 2,6-$F_2$ | O | " | " | " | |
| 391 | 2-Cl | O | " | —$OCF_2CHClF$ | " | |
| 392 | 2-F | O | " | " | " | |
| 393 | 2,6-$F_2$ | O | " | " | " | |
| 394 | 2-Cl | O | " | —$OCF_2CHFCF_3$ | " | |
| 395 | 2-F | O | " | " | " | |
| 396 | 2,6-$F_2$ | O | " | " | " | |
| 397 | 2-Cl | O | 3-$COOCH_3$ | —$OCHF_2$ | " | |
| 398 | 2-F | O | " | " | " | |
| 399 | 2,6-$F_2$ | O | " | " | " | |
| 400 | 2-Cl | O | " | —$OCF_3$ | " | |
| 401 | 2-F | O | " | " | " | |
| 402 | 2,6-$F_2$ | O | " | " | " | |
| 403 | 2-Cl | O | " | —$OCF_2CHF_2$ | " | |
| 404 | 2-F | O | " | " | " | |
| 405 | 2,6-$F_2$ | O | " | " | " | |
| 406 | 2-Cl | O | " | —$OCF_2CHClF$ | " | |
| 407 | 2-F | O | " | " | " | |
| 408 | 2,6-$F_2$ | O | " | " | " | |
| 409 | 2-Cl | O | 3-$COOCH_3$ | —$OCF_2CHFCF_3$ | Cl | |
| 410 | 2-F | O | " | " | " | |
| 411 | 2,6-$F_2$ | O | " | " | " | |
| 412 | 2-Cl | O | 3-Cl; 5-$COOCH_3$ | —$OCHF_2$ | " | |
| 413 | 2-F | O | " | " | " | |
| 414 | 2,6-$F_2$ | O | " | " | " | |
| 415 | 2-Cl | O | " | —$OCF_3$ | " | |
| 416 | 2-F | O | " | " | " | |
| 417 | 2,6-$F_2$ | O | " | " | " | |
| 418 | 2-Cl | O | " | —$OCF_2CHF_2$ | " | |
| 419 | 2-F | O | " | " | " | |
| 420 | 2,6-$F_2$ | O | " | " | " | |
| 421 | 2-Cl | O | " | —$OCF_2CHClF$ | " | |
| 422 | 2-F | O | " | " | " | |
| 423 | 2,6-$F_2$ | O | " | " | " | |
| 424 | 2-Cl | O | " | —$OCF_2CHFCF_3$ | " | |
| 425 | 2-F | O | " | " | " | |
| 426 | 2,6-$F_2$ | O | " | " | " | |
| 427 | 2-Cl | S | 3,5-$Cl_2$ | —$OCHF_2$ | " | |
| 428 | 2-F | S | " | " | " | |
| 429 | 2,6-$F_2$ | S | " | " | " | |
| 430 | 2-Cl | S | " | —$OCF_3$ | " | |
| 431 | 2-F | S | " | " | " | |
| 432 | 2,6-$F_2$ | S | " | " | " | |
| 433 | 2-Cl | S | " | —$OCF_2CHF_2$ | " | |
| 434 | 2-F | S | " | " | " | |

TABLE 8-continued

Structure: (Q¹)r-phenyl-C(=O)-NH-C(=Y²)-NH-phenyl(3,(Q²)s,5)-O-pyridyl(R¹¹, N→O, R¹⁰)

| Ex. No. | (Q¹)r | Y² | (Q²)s | R¹⁰ | R¹¹ | m.p. (°C.) |
|---|---|---|---|---|---|---|
| 435 | 2,6-F₂ | S | " | " | " | |
| 436 | 2-Cl | S | " | —OCF₂CHClF | " | |
| 437 | 2-F | S | " | " | " | |
| 438 | 2,6-F₂ | S | " | " | " | |
| 439 | 2-Cl | S | " | —OCF₂CHFCF₂ | " | |
| 440 | 2-F | S | " | " | " | |
| 441 | 2,6-F₂ | S | " | " | " | |

TABLE 9

Structure: (Q¹)r-phenyl-G-phenyl(2,6-Cl₂)-O-pyridyl(Cl, N→O, R¹⁰)

| Ex. No. | (Q¹)r | G | R¹⁰ | m.p. (°C.) |
|---|---|---|---|---|
| 442 | 2-Cl | —C(OC₂H₅)=N—C(=O)—NH— | —OCHF₂ | |
| 443 | 2,6-F₂ | | —OCHF₂ | |
| 444 | 2,6-F₂ | | —OCHF₂ | |
| 445 | 2-Cl | | —OCF₃ | |
| 446 | 2-F | " | —OCF₃ | |
| 447 | 2,6-F₂ | " | —OCF₃ | |
| 448 | 2-Cl | " | —OCF₂CHF₂ | |
| 449 | 2-F | " | —OCF₂CHF₂ | |
| 450 | 2,6-F₂ | " | —OCF₂CHF₂ | |
| 451 | 2-Cl | " | OCF₂CHClF | |
| 452 | 2-F | " | OCF₂CHClF | |
| 453 | 2,6-F₂ | " | OCF₂CHClF | |
| 454 | 2-Cl | " | OCF₂CHFCF₃ | |
| 455 | 2-F | " | OCF₂CHFCF₃ | |
| 456 | 2,6-F₂ | " | OCF₂CHFCF₃ | |
| 457 | 2-Cl | (dioxotriazine ring) | OCHF₂ | |
| 458 | 2-F | | OCHF₂ | |
| 459 | 2,6-F₂ | | OCHF₂ | |
| 460 | 2-Cl | | OCF₃ | |
| 461 | 2-F | " | OCF₃ | |
| 462 | 2,6-F₂ | " | OCF₃ | |
| 463 | 2-Cl | " | OCF₂CHF₂ | |
| 464 | 2-F | " | OCF₂CHF₂ | |
| 465 | 2,6-F₂ | " | OCF₂CHF₂ | |
| 466 | 2-Cl | | OCF₂CHFlF | |
| 467 | 2-F | | OCF₂CHFlF | |
| 468 | 2,6-F₂ | | OCF₂CHFlF | |
| 469 | 2-Cl | | OCF₂CHFCF₃ | |
| 470 | 2-F | " | OCF₂CHFCF₃ | |
| 471 | 2,6-F₂ | " | OCF₂CHFCF₃ | |

TABLE 10

Structure: (Q¹)r-phenyl-C(=O)-NH-C(=Y²)-NH-pyridyl(Cl, N→O, R¹⁰)

| Ex. No. | (Q¹)r | Y² | R¹⁰ | m.p. (° C.) |
|---|---|---|---|---|
| 472 | 2-Cl | O | OCHF₂ | |
| 473 | 2-F | O | OCHF₂ | |
| 474 | 2,6-F₂ | O | OCHF₂ | |
| 475 | 2-Cl | O | OCF₃ | |
| 476 | 2-F | O | OCF₃ | |
| 477 | 2,6-F₂ | O | OCF₃ | |
| 478 | 2-Cl | O | OCF₂CHF₂ | |
| 479 | 2-F | O | OCF₂CHF₂ | |
| 480 | 2,6-F₂ | O | OCF₂CHF₂ | |
| 481 | 2-Cl | O | OCF₂CHClF | |
| 482 | 2-F | O | OCF₂CHClF | |
| 483 | 2,6-F₂ | O | OCF₂CHClF | |
| 484 | 2-Cl | O | OCF₂CHFCF₃ | |
| 485 | 2-F | O | OCF₂CHFCF₃ | |
| 486 | 2,6-F₂ | O | OCF₂CHFCF₃ | |
| 487 | 2-Cl | S | OCHF₂ | |
| 488 | 2-F | S | OCHF₂ | |
| 489 | 2,6-F₂ | S | OCHF₂ | |
| 490 | 2-Cl | S | OCF₃ | |
| 491 | 2-F | S | OCF₃ | |
| 492 | 2,6-F₂ | S | OCF₃ | |
| 493 | 2-Cl | S | OCF₂CHF₂ | |
| 494 | 2-F | S | OCF₂CHF₂ | |
| 495 | 2,6-F₂ | S | OCF₂CHF₂ | |
| 496 | 2-Cl | S | OCF₂CHClF | |
| 497 | 2-F | S | OCF₂CHClF | |
| 498 | 2,6-F₂ | S | OCF₂CHClF | |
| 499 | 2-Cl | S | OCF₂CHFCF₃ | |
| 500 | 2-F | S | OCF₂CHFCF₃ | |
| 501 | 2,6-F₂ | S | OCF₂CHFCF₃ | |

BIOLOGICAL EXAMPLES

Example I

Spodoptera test

Larvae of the African cotton worm (*Spodoptera littoralis* L III) and Petri dishes containing an agar-based diet were treated in a spraying apparatus with an active compound preparation of the desired concentration. The larvae were placed on the agar diet after the spray coating had dried.

After the desired time (L III until hatching of the moths), the destruction of the caterpillars or the hatching of the moths was determined in %. 100% here denotes that all the caterpillars were killed or that no moths hatch from the caterpillars.

In this test, the compounds of the Examples 1, 2, 82, 83, 90, 104, 105, 145 and 147 exhibited 100% activity at 100 ppm of active compound in the spray liquor.

Example II

Musca test

Housefly larvae (*Musca domestica*), 24 hours old, were placed on a fly diet which had previously been treated with an active compound preparation of the desired concentration.

After the desired time (L I to hatching of the flies), the destruction of the larvae or the hatching of the flies was determined in %. 100% here denotes that all larvae were destroyed or that no flies hatched from the pupae.

The compounds of the Examples 1, 2, 82, 83, 90, 104 and 105 achieved 100% activity at 100 ppm of active compound.

Example III

Aedes test

Aqueous active compound preparations of the desired concentration were placed in conical flasks and yellow-fever mosquito larvae (*Aedes aegypti*), 24 hours old, were subsequently placed in the flasks.

After the desired time (to the hatching of the mosquitoes), the destruction of the larvae or the hatching of the mosquitoes was determined in %. 100% here denotes that all larvae were destroyed or that no mosquitoes hatched.

The compounds of the Examples 1, 2, 82 and 104 achieved 100% activity at 100 ppm of active compound.

Example IV

Oncopeltus test

Larvae of a cotton bug (*Oncopeltus fasciatus* L III) were placed in a plastic beaker together with a dental pellet which had previously been treated with an active compound preparation of the desired concentration.

after the desired time (L III to imago), the destruction of the larvae or the hatching of the imago was determined in %. 100% here denotes that all larvae were destroyed or that no imago hatched from the final larval stage.

The compounds according to Examples 1, 2, 82, 90 and 104 achieved 100% activity at 100 ppm of active compound.

Example V

Heliothis test

Larvae of the American tobacco budworm (*Heliothis virescens*, L III) and Petri dishes containing an agar-based diet were treated in a spraying apparatus with an active compound preparation of the desired concentration. The larvae were placed on the agar diet after the spray coating had dried.

After the desired time (7 days, molting stages L III to L IV), the destruction of the caterpillars was determined in %. 100% here denotes that all caterpillars were destroyed.

The compounds according to Examples 1, 2, 82, 83, 90, 104 and 105 achieved 100% activity at 100 ppm of active compound.

Example VI

Trialeurodes test

Bean plants (*Phaseolus vulgaris*), heavily infested with whitefly (*Trialeurodes vaporariorum*, eggs), were sprayed with active compound of the desired concentration in the spray liquor until dripping commenced. After placing the plants in a greenhouse at 20°–25° C. and 40°–50% relative humidity, microscopic inspection was carried out after 14 days.

The compounds of the Examples 1, 2, 82, 83, 90 and 105 achieved 100% activity at 20 ppm of active compound.

The disclosure of the commonly assigned U.S. application Ser. No. 944,324 which corresponds to West German Patent Application P No. 35 45 571.3, is entitled "Heterocyclic phenyl ethers, processes for the preparation thereof, and herbicidal agents containing same" (attorney docket no. 514410-2452) and is filed concurrently herewith is hereby incorporated by reference. Also, the disclosure of the commonly assigned U.S. application Ser. No. 944,547 which corresponds to West German Patent Application No. P 35 45 570.5, is entitled "Novel pyridine derivatives and the N-oxides thereof, processes for the preparation thereof, and the use thereof as intermediates" and is filed concurrently herewith is hereby incorporated by reference.

We claim:

1. A compound of formula I

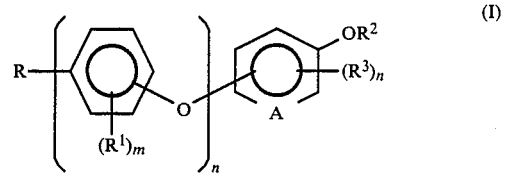

or an agriculturally acceptable salt thereof in which

A is N or N→O,

R is a radical of formula

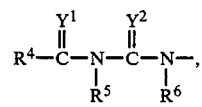

$R^1$, in each case independently of one another, is halogen or is $(C_1$–$C_6)$-alkyl, $(C_2$–$C_6)$-alkenyl, $(C_2$–$C_6)$-alkynyl, $(C_1$–$C_6)$-alkoxy, $(C_1$–$C_6)$-alkoxycarbonyl or $(C_1$–$C_6$-alkyl)-carbonyl which are unsubstituted or mono- or polysubstituted by halogen, or is nitro, cyano or carboxyl, $R^2$ is halogenated $(C_1$–$C_6)$-alkyl, halogenated $(C_2$–$C_6)$-alkenyl or halogenated $(C_2$–$C_6)$-alkynyl, $R^3$, in each case independently of one another, is halogen, $R^4$ is phenyl which is unsubstituted or substituted by halogen, $(C_1$–$C_3)$-alkyl, $(C_1$–$C_3)$-alkoxy, halo($C_1$–$C_3)$-alkyl or halo($C_1$–$C_3)$-alkoxy, $R^5$ is hydrogen, $(C_1$–$C_6)$-alkoxy, $(C_1$–$C_6)$-alkylthio, benzyl, halogenated $(C_1$–$C_6)$-alkoxy, halogenated $(C_1$–$C_6)$-alkylthio or halogenated benzyl, $R^6$ is hydrogen or is $(C_1-C_6)$-alkyl, $(C_1-C_6)$-alkylthio or $(C_1-C_6)$-alkylsulfonyl which all are unhalogenated or is phenylthio or phenylsulfonyl which is substituted by $(C_1-C_6)$-alkyl, $(C_1-C_6)$-alkoxy, $(C_1-C_6)$-alkoxycarbonyl, halogenated $(C_1-C_6)$-alkyl, halogenated $(C_1-C_6)$-alkoxy, halogenated $(C_1-C_4)$-alkoxycarbonyl, halogen, nitro or cyano, or is phosphoryl or thiophosphoryl which are both substituted by two radicals selected from the group consisting of $(C_1-C_6)$-alkoxy, $(C_1-C_6)$-alkylthio, amino, $(C_1-C_6)$-alkylamino or di-$(C_1-C_6$-alkyl)-amino, $Y^1$ and $Y^2$, are the same or different and each is O or S, n, in each case independently of one another, is 0, 1 or 2, and m is 0, 1, 2 or 3.

2. A compound of formula I as claimed in claim 1, in which

A is N,

R is a radical of formula

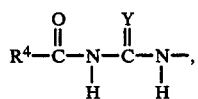

$R^1$, in each case independently of one another, is halogen, or is $(C_1-C_6)$-alkyl or $(C_1-C_6)$-alkoxycarbonyl which are unsubstituted or mono- or polysubstituted by halogen, $R^2$ is halogenated $(C_1-C_6)$-alkyl, halogenated $(C_2-C_6)$-alkenyl or halogenated $(C_2-C_6)$-alkynyl, $R^3$, in each case independently of one another, is halogen, $R^4$ is phenyl which is unsubstituted or substituted by halogen, $(C_1-C_3)$-alkyl, $(C_1-C_3)$-alkoxy, halo($C_1-C_3$)-alkyl or halo($C_1-C_3$)-alkoxy, Y is O or S, n, in the case of the phenoxy radical, is 0 or 1 and, in the case of the $R^3$ radical, is 0, 1 or 2, and m is 0, 1, 2 and 3.

3. A compound of formula I as claimed in claim 2, in which $R^1$ is halogen in the 2, 3 or 5 position of the phenoxy ring relative to the position of R, or halo-$(C_1-C_6)$-alkyl or $(C_1-C_3)$-alkoxycarbonyl, in each case in the 3 or 5 position of the phenoxy ring, $R^2$ is halo($C_1-C_3$)-alkoxy, $R^3$ is F, Cl or Br, and $R^4$ is phenyl which is substituted by halogen, and A Y, n and m have the meanings specified in claim 2.

4. A compound as claimed in claim 3, in which $R^4$ is phenyl which is substituted by halogen in the 2 or 6 position.

5. The compound as claimed in claim 1 which is N-4-((3-chloro-5-1,1-difluoroethoxy-2-pyridyloxy)-3,5-dichlorophenol)-N'-2-fluorobenzoylurea.

6. Insecticidal, acaricidal, nematicidal and molluskicidal compositions which contain an effective amount of a compound of formula I as claimed in claim 1 and an inert carrier.

7. A process for combating noxious insects, acarides, nematodes and mollusks which comprises applying an effective amount of a compound of formula I as claimed in claim 1 to these pests or to plants infested by same.

* * * * *